United States Patent [19]

Egger

[11] Patent Number: Plant 7,438

[45] Date of Patent: Feb. 5, 1991

[54] **GAZANIA PLANT CALLED *GAZANIA RIGENS* "B"**

[75] Inventor: Janet N. Egger, Ventura, Calif.

[73] Assignee: Mitsuwa Nursery, Inc., Moorpark, Calif.

[21] Appl. No.: 471,512

[22] Filed: Jan. 29, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Roylance, Abrams, Berdo & Goodman

[57] ABSTRACT

A perennial hybrid Gazania groundcover which is distinguished by the color of its flowers, a multicolor yellow orange with white tips that appears pastel orange when viewed from a distance, and its green trailing foliage. In addition, the invention plant is floriferous, vigorous, and disease and frost tolerant.

1 Drawing Sheet

BACKGROUND TO THE INVENTION

The present invention relates to a new and distinctive cultivar of Gazania plant botanically known as *Gazania rigens* hybrid and referred to for patenting purposes with the name "B". *Gazania rigens* "B" was developed by controlled breeding using *Gazania rigens* "A" (patent applied for) as the seed parent and *Gazania rigens* 'Mitsuwa White' (U.S. Plant Pat. No. 5,797) as the pollen parent.

BRIEF DESCRIPTION OF THE INVENTION

*Ganzania rigens* "B" is perennial trailing groundcover with good vigor, hardiness, deep green leaves and flowers that are a multicolored yellow orange with white tips and which appear a pastel orange color when viewed from a distance (called in the specification and claim hereinafter "Multicolor"). *Gazania rigens* "B" blooms from February to December in Southern California. The Multicolor and the pastel orange appearance of the flowers are unique in trailing green leaf Gazania groundcovers and are believed to be substantial steps forward for this plant in the groundcover industry.

DESCRIPTION OF THE DRAWING

The accompanying color photograph, forming a part of this disclosure, was taken in Summer 1989 in a greenhouse in Moorpark, Calif., and shows a close-up of *Gazania rigens* "B" growing in a five gallon pot; the view being more or less straight down onto the plant. The photograph shows the typical flower and foliage forms and colors as true as are resonably possible in this type of color photograph.

Comparison of *Gazania rigens* "B" with other Commercial Orange Gazania Groundcovers The primary distinguishing feature of *Gazania rigens* "B" is its Multicolor flower. This color is new to trailing green leaf Gazania groundcovers; that is, to the inventor's knowledge, *Gazania rigens* "B" is the first Gazania with Multicolor flowers, green leaves, and a trailing habit.

To the inventor's knowledge, the only other orange flowering Gazanias with trailing habits and green foliage have yellow orange or deep orange flowers. These are *Gazania rigens* 'Mitsuwa Orange' (U.S. Plant Pat. No. 5,796) and *Gazania rigens* "A", the seed parent (patent applied for). This U.S. Plant Pat. No. 5,796 was issued Nov. 4, 1986 and is owned in common with the present invention.

Compared to *Gazania rigens* 'Mitsuwa Orange', *Gazania rigens* "B" is more vigorous and its leaves are larger and a deeper green. The flower head are larger, with the unique Multicolor rather than a yellow orange color. The flower heads of *Gazania rigens* "B" have a black ring around the flower center, while those of *Gazania rigens* 'Mitsuwa Orange' do not. A similar black ring feature is found, however, around the flower centers of *Gazania rigens* "A".

Compared to *Gazania rigens* "A", *Gazania rigens* "B" is even more vigorous and its leaves are larger. The flower heads are also larger and are Multicolor rather than deep orange. Both have a black ring around the flower center and both are floriferous. *Gazania rigens* "B" is even more frost hardy than *Gazania rigens* "A".

DETAILED DESCRIPTION

The following is a detailed description of *Gazania rigens* "B" based on plants produced under commercial practices outdoors at Mitsuwa Nursey, Moorpark, Calif. Color references are made to The Royal Horticultural Society Colour Chart except where the context indicates a term having its ordinary dictionary meaning.

Parentage: A controlled cross with *Gazania rigens* "A" as the seed parent and *Gazania rigens* 'Mitsuwa White' as the pollen parent.

Plant form: Plants are a vigorous growing, trailing groundcover.

Habit of Growth: Plants are decumbent, spreading rapidly to approximate 1 meter in diameter. Plants form a dense carpet to approximate 16 cm in height.

Foliage: Foliage is a medium green with simple alternate leaves.

(1) *Size.*—Mature leaves are approximately 10–12 cm in length and 14 mm in width at the widest point.

(2) *Shape.*—Oblanceolate.

(3) *Texture.*—The top side of the leaf is glabrous; the bottom side is density white tomentose.

(4) *Margin.*—Entire, subrevolute.

(5) *Color.*—Young foliage, top side — 137 C. Young foliage, underside — 155 D. Mature foliage, top side — 137 A and B. Mature foliage, underside — 155 D.

Flowering description: The flowers are Multicolor with a black ring around the flower center at the base. The plants are very floriferous.

(1) *Habit.*—The flower heads arise from leaf axils on peduncles to approximately 15–20 cm in length.

(2) *Season of bloom.*—Varies with the climate. In Moorpark, Calif., heavy bloom occurs from approximately late February to early December.

(3) *Flower parts.*—(a) Flower head measures 7–7½ cm across. (b) Ray petals measure approximate 4 cm in length. The base of each petal has a black oval shaped spot measuring approximately 3–4 mm across and with one white dot in the middle. This black oval shaped spot forms the band or ring at the flower base. The underside of each ray petal has a dark section down the center between the two main veins.

(4) *Color.*—Disc flowers (closed)-24 A. Ray petal, topside tip-11 D to 14 D. Ray petal, topside middle to spot-14 B. Ray petal, topside spot 202 A. Ray petal, topside base below spot-23 A. Ray petal, bottomside edge-12 D. Ray petal, bottomside dark section-186 C to 202 A. Ray petal, bottomside spot-107 A.

Disease Resistance: No disease problems noted.

Hardiness: In Winter of 1987 the experimental Gazania trail field in Moorpark, Calif., were badly frost damage. Many of the Gazania varieties died and most died back. Almost all had leaf burn. *Gazania rigens* "B" had no damage.

Propagation: Asexual reproduction by steam cuttings has shown that the unique features of this new Gazania are stable and are reproduced true to type in successive propagation. *Gazania rigens* "B" roots rapidly under warm conditions.

I claim:

1. A new and distinct cultivar of Gazania as described and illustrated, particularly characterized by its floriferous showy Multicolor flowers, green foliage, vigorous growth, and trailing habit.

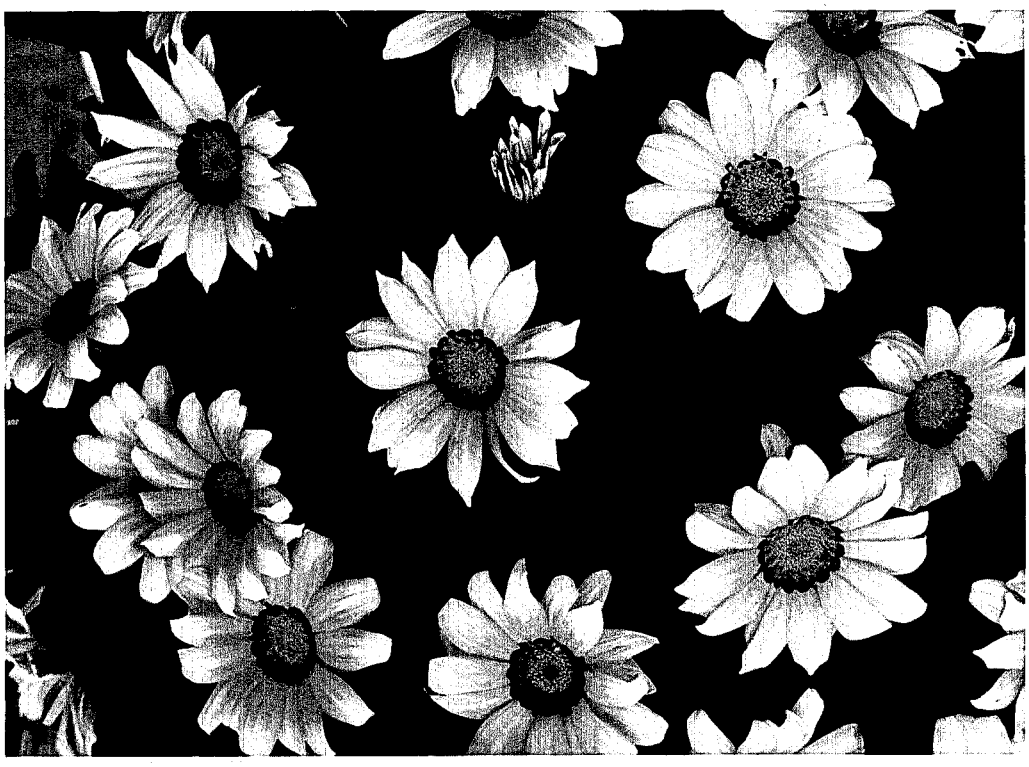

* * * * *